(12) United States Patent
Yoshida et al.

(10) Patent No.: US 7,053,225 B2
(45) Date of Patent: May 30, 2006

(54) INTERMEDIATES AND IMPROVED PROCESSES FOR THE PREPARATION OF NEPLANOCIN A

(75) Inventors: Naoyuki Yoshida, Ichihara (JP); Kunio Ogasawara, Sendai (JP)

(73) Assignee: Chisso Corporation, Osaka-Fu (JP)

( * ) Notice: Subject to any disclaimer, the term of this patent is extended or adjusted under 35 U.S.C. 154(b) by 513 days.

(21) Appl. No.: 10/369,686

(22) Filed: Feb. 21, 2003

(65) Prior Publication Data

US 2003/0162282 A1    Aug. 28, 2003

Related U.S. Application Data

(62) Division of application No. 09/849,356, filed on May 7, 2001, now Pat. No. 6,642,424, which is a division of application No. 09/318,435, filed on May 25, 1999, now Pat. No. 6,265,209.

(30) Foreign Application Priority Data

May 25, 1998    (JP)    ................... 10-158687

(51) Int. Cl.
*C07D 307/77*    (2006.01)
*C12P 41/00*    (2006.01)

(52) U.S. Cl. ..................... 549/457; 435/280

(58) Field of Classification Search .............. None
See application file for complete search history.

(56) References Cited

U.S. PATENT DOCUMENTS 5,300,664 A    4/1994    Takano et al.

OTHER PUBLICATIONS

"Lipase-Mediated Kinetic Resolution of a Synthetic Equivalent of 2-Hydroxymethylcyclopentadien-5-ol", by Yoshida et al., Tetrahedron: Asymmetry 9 (1998), pp. 3325-3329.
"A Concise Synthesis of (-)-Neplanocin A", by Yoshida et al., Tetrahedron Letters 39 (1988), pp. 4677-4678.
"Total Synthesis of (-)-Neplanocin A from L-Ribulose", by Vandewalle et al., Synlett (Dec. 1991), pp. 921-922.
"Synthesis of (-)-Neplanocin A via C-H Insertion of Alkylidenecarbene", by Ohira et al., Tetrahedron Letters, vol. 36, No. 9 (1995), pp. 1537-1538.
"An Enantio- and Diastereo-Controlled Synthesis of (-) Neplanocin A and its 2,3-Di-Epi-Isomer", by Trost et al., Tetrahedron Letters, vol. 38, No. 10 (1997), pp. 1707-1710.
"Nucleophilic Eliminative Ring Fission of Bridgehead Substituted 1,3-Bishomocubyl Acetates", by Klunder et al., Tetrahedron, vol. 41, No. 5 (1985), pp. 963-973.

*Primary Examiner*—Sandra E. Saucier
(74) *Attorney, Agent, or Firm*—McDermott Will & Emery LLP

(57) ABSTRACT

Intermediate compounds, including 2-(t-butyldimethylsilyloxymethyl)-3,4-[(dimethylmethylene)dioxy]-5-hydroxy-tricyclo[5.2.1.0$^{2,6}$]dec-8-ene, which are useful for the synthesis of neplanocin A having strong antitumor activity. Improved processes for the preparation of neplanocin A, starting from optically active 2-hydroxymethyl-5-hydroxy-tricyclo[5.2.1.0$^{2,6}$]deca-3,8-diene and via a key step comprising a retro-Diels-Alder reaction of the above intermediate.

2 Claims, No Drawings

INTERMEDIATES AND IMPROVED PROCESSES FOR THE PREPARATION OF NEPLANOCIN A

RELATED APPLICATIONS

This application, concurrently filed with divisional application Ser. Nos. 10/369,510, 10/369,560 and 10/369,532, is a divisional of application Ser. No. 09/849,356, filed May 7, 2001, now U.S. Pat. No. 6,642,424, which is a divisional of application Ser. No. 09/318,435, filed May 25, 1999, now U.S. Pat. No. 6,265,209.

This invention relates to compounds, including 2-(t-butyldimethylsilyloxymethyl)-3,4-[(dimethylmethylene)-dioxy]-5-hydroxy-tricyclo[5.2.1.0$^{2,6}$]dec-8-ene and the analogues thereof, which are useful as intermediates for the synthesis of neplanocin A having strong antitumor activity. The invention also relates to improved processes for the preparation of neplanocin A.

BACKGROUND OF THE INVENTION

Neplanocin A is represented by the following formula and one of carbanucleosides having strong antitumor activity, but it is not itself a sufficient drug for the clinical treatment of cancer, because of its strong adverse effect.

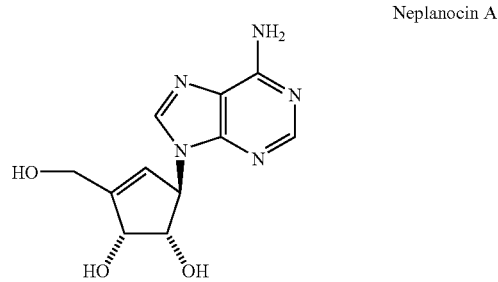

Neplanocin A

Nevertheless, there have been desired improved methods for efficiently preparing neplanocin A and related compounds.

Vandewalle et al. (Synlett, December 1991, 921–922) disclose the synthesis of (−)-neplanocin A starting from L-ribulose in 14 steps and in 15% overall yield. Ohira et al. (Tetrahedron Letters, vol. 36, No. 9, pp. 1537–1538, 1995) disclose the synthesis of (−)-neplanocin A starting from D-ribose modified with the protecting group in 9 steps and in 12% overall yield. Trost et al. (Tetrahedron Letters, vol. 38, No. 10, pp. 1707–1710, 1997) disclose the stereoselective synthesis of (−)-neplanocin A using an asymmetric catalyst in 13 steps and in 4% overall yield. Thus, the above prior processes require more improvement in the process step and yield.

SUMMARY OF THE INVENTION

The present invention provides a group of intermediates useful for the synthesis of neplanocin A and related compounds which improve our flexibility in exploring structural variation of carbanucleosides having potential use including chemotherapeutic agents.

The invention also relates to improved processes for the preparation of neplanocin A in short process step and in high yield, starting from a compound of the following formula (1) and via a compound of the following formula (6).

DETAILED DESCRIPTION OF THE INVENTION

The present invention provides new class of the compounds useful as intermediates for the synthesis of neplanocin A, which includes the compounds of the following formulas:

Formula (1)

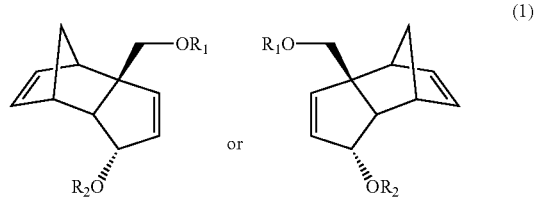

wherein $R_1$ and $R_2$ are independently hydrogen or an alkanoyl group of 2–20 carbons;

Formula (2)

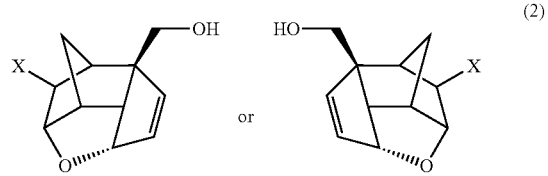

wherein X is halogen;

Formula (3)

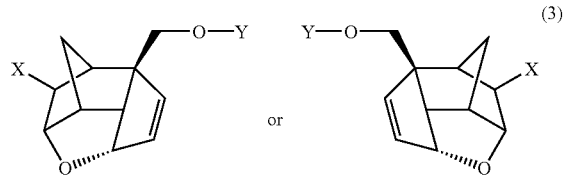

wherein X is halogen and Y is a protecting group;

Formula (4)

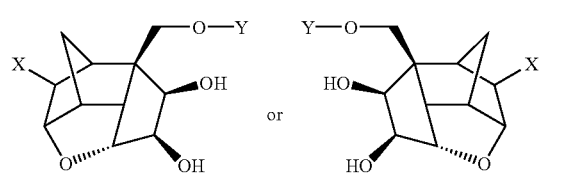

wherein X is halogen and Y is a protecting group;

Formula (5)

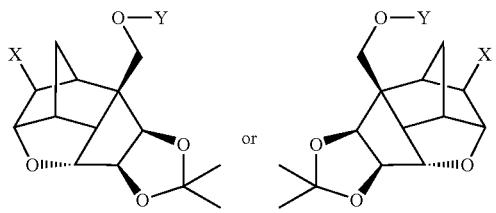

wherein X is halogen and Y is a protecting group;

Formula (6)

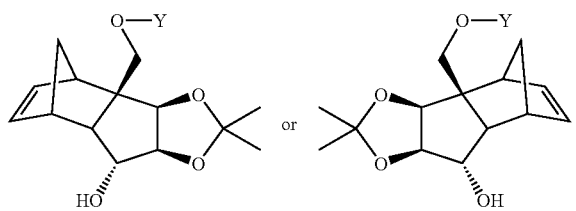

wherein Y is a protecting group;

Formula (7)

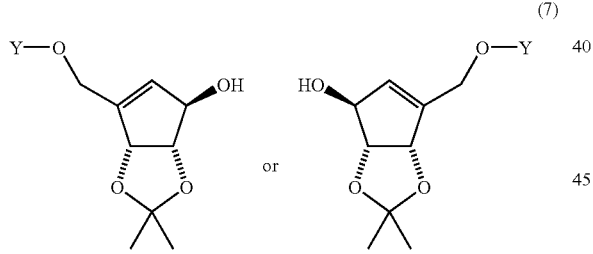

wherein Y is a protecting group;

Formula (8)

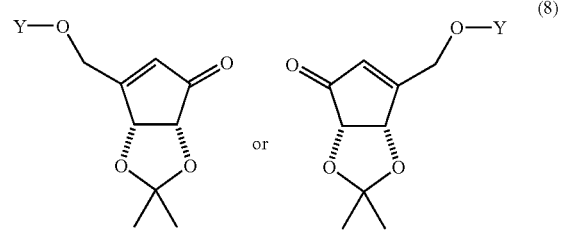

wherein Y is a protecting group;

Formula (9)

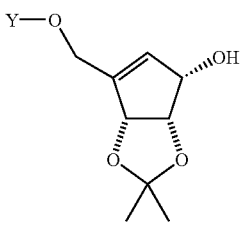

wherein Y is a protecting group;

Formula (10)

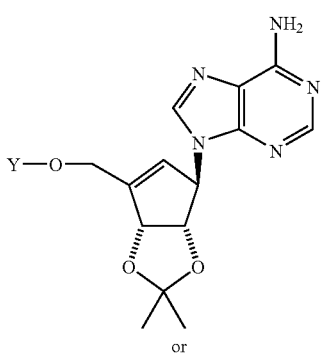

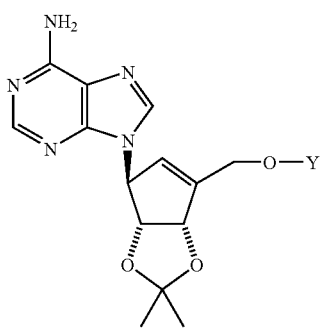

wherein Y is a protecting group.

Examples of the alkanoyl group of 2–20 carbons for $R_1$ and $R_2$ include, but are not limited to, acetyl, propionyl, butyryl, isobutyryl, valeryl, isovaleryl, pivaloyl, lauroyl, myristoyl, palmitoyl, stearoyl, caproyl, enanthoyl, capryloyl and icosanoyl. Examples of the halogen for X are Cl, Br and I.

The protecting groups for Y can include any group known in the art of organic synthesis for the protection of hydroxyl groups. Examples of such protecting group include, but are not limited, to trimethylsilyl, triethylsilyl, t-butyldimethylsilyl (TBS), t-butyldiphenylsilyl, methoxymethyl, methoxyethoxymethyl, t-butyl, benzyl, triphenylmethyl, isopropyldimethylsilyl, tribenzylsilyl and triisopropylsilyl.

Specific compounds within formulas (2)–(10) are represented by the following respective formulas (2a)–(10a):

wherein TBS stands for t-butyldimethylsilyl.

The present invention also provides a process for the preparation of neplanocin A which comprises the steps of:

(a) reacting a compound of formula (1')

with a halogenating agent, to form a compound of formula (2)

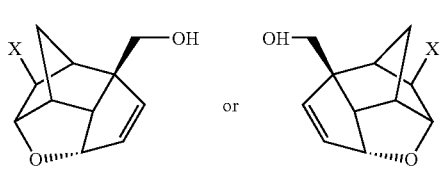

wherein X is halogen;

(b) reacting the compound (2) with an agent for the protection of hydroxyl groups, to form a compound of formula (3)

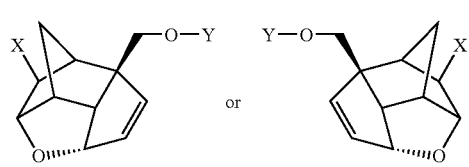

wherein X is as defined above and Y is a protecting group;

(c) treating the compound (3) with an oxidizing agent, to form a compound of formula (4)

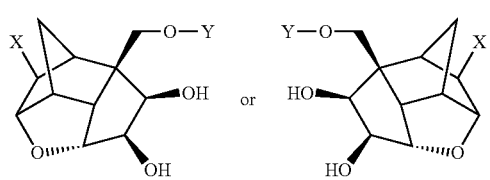

wherein X and Y are as defined above;

(d) reacting the compound (4) with a ketalizing agent, to form a compound of formula (5)

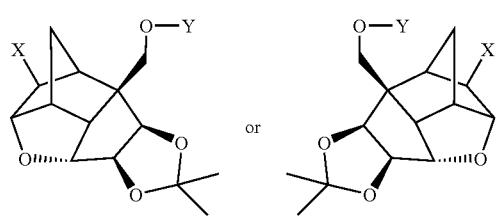

wherein X and Y are as defined above;

(e) treating the compound (5) with a dehalogenating agent, to form a compound of formula (6)

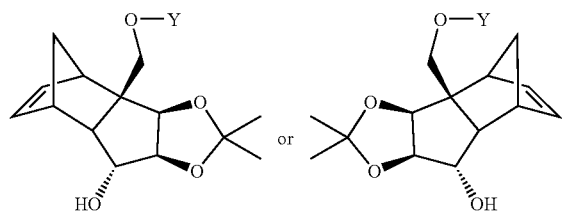

wherein Y is as defined above;

(f) subjecting the compound (6) to a retro-Diels-Alder reaction, to form a compound of formula (7)

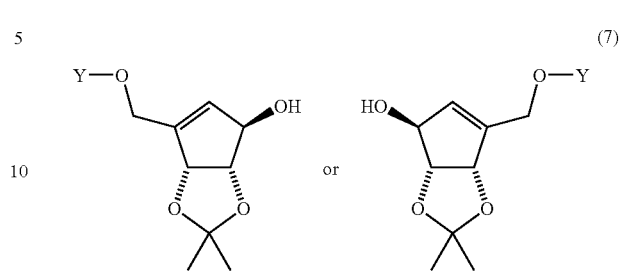

wherein Y is as defined above;

(g) treating the compound (7) with an oxidizing agent, to form a compound of formula (8)

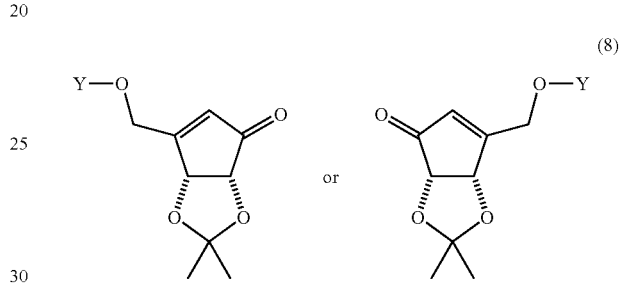

wherein Y is as defined above;

(h) reducing the compound (8) with a reducing agent, to form a compound of formula (9)

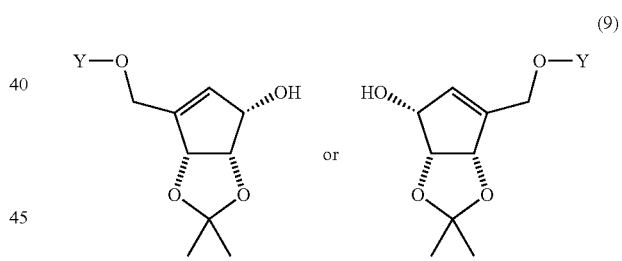

wherein Y is as defined above;

(i) subjecting the compound (9) to a Mitsunobu reaction, to form a compound of formula (10)

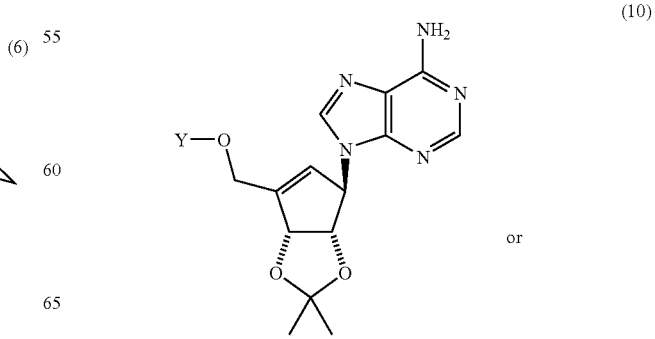

-continued

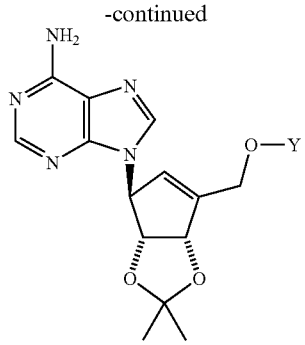

wherein Y is as defined above, followed by deprotection.

The process for the preparation of neplanocin A is illustrated below, in order of steps (a) to (i).

Step (a)

Depending on the halogenating agent and the solvent used, the reaction may be carried out at a temperature of about −20 to 20° C., preferably about 0° C., for about 1 to 10 hrs, preferably 2 hrs. As a reaction solvent may be used a halogenated hydrocarbon solvent such as dichloromethane, chloroform and dichloroethane. The halogenating agents such as brominating, chlorinating and iodinating agents are well known in the art of organic synthesis. Examples of such halogenating agents include, but are not limited, to HBr, diphos-Br$_2$, N-bromosuccinimide (NBS), thionyl bromide, HCl, diphos-Cl$_2$, N-chlorosuccinimide (NCS) and thionyl chloride.

Step (b)

The agents for the protection of hydroxyl groups (called "protecting agent" hereafter) may be selected from any agent known in the art of organic synthesis for the protection of hydroxyl groups, for example, but not limited to halides including chlorides or bromides of trimethylsilyl, triethylsilyl, t-butyldimethylsilyl, t-butyldiphenylsilyl, methoxymethyl, methoxyethoxymethyl, t-butyl, benzyl, triphenylmethyl, isopropyldimethylsilyl, tribenzylsilyl, triisopropylsilyl or the like.

Depending on the protecting agent and solvent used, the reaction may be carried out at a temperature of about −20 to 40° C., for about 10 to 20 hrs. As a solvent may be used a base such as imidazole, benzimidazole, triethylamine, pyridine and hexamethylene disilazane. A base for fixation of free halogenated hydrogen may also be used as the solvent. Where the protecting agent is each kind of silyl chlorides and methoxyethoxymethyl halides, the above-mentioned bases are used. Where the protecting agent is benzyl halides and methoxymethyl halides, sodium hydride is used as the base. Where the hydroxyl group is protected with t-butyl group, the reaction is carried out with isobutene in the presence of an acid type catalyst such as sulfuric acid.

Step (c)

The oxidizing agents used may be selected from any of a variety of the agents known in the art of synthetic organic chemistry, for example, but not limited to, osmium tetraoxide, potassium permanganate, lead tetraacetate, ruthenium tetraoxide and selenium dioxide+hydrogen peroxide, with osmium tetraoxide being most preferred.

Depending on the oxidizing agent and solvent used, the reaction may be carried out at a temperature of about −20 to 40° C., for about 1 to 30 hrs. As a reaction solvent may be used a polar solvent such as water and tetrahydrofuran (THF). Where the oxidizing agent is catalytically used, the reaction is carried out in the presence of an oxygen source such as methylmorpholine N-oxide.

Step (d)

The ketalizing agents may be selected from acetals such as 2,2-dimethoxypropane, 2,2-diethoxypropane or the like.

Depending on the ketalizing agent, solvent and catalyst used, the reaction may be carried out at a temperature of about −20 to 40° C., preferably around room temperature, for about 15 to 30 hrs. The reaction solvents which may be used are relatively low boiling point solvents (excluding alcohols) among conventional solvents, such as acetone, methyl ethyl ketone, hydrocarbons, halogenated hydrocarbons, diethyl ether, diisopropyl ether and THF. The catalysts which may be used in the reaction are acid type catalysts such as hydrochloric acid, ammonium chloride, p-toluenesulfonic acid, pyridinium p-toluenesulfonate, aluminum chloride and an acid type ion-exchange resin.

Step (e)

The dehalogenating agents used may be selected from any of a variety of the agents known in the art of synthetic organic chemistry, for example, but not limited to, active zinc dust, magnesium, sodium, palladium, sodium iodide and potassium iodide.

Depending on the dehalogenating agent and solvent used, the reaction may be carried out under heat at reflux, for about 5 to 20 hrs. The reaction solvents which may be used are alcohols such as methanol, ethanol, propanol and isopropanol, with methanol being preferable.

Step (f)

The retro-Diels-Alder reaction used here refers to thermal dissociation of Diels-Alder adducts, occurring most readily when one or both fragments are particularly stable (see, Organic Name Reactions attached to The Merck Index, 12th Edn.) The reaction may be carried out under heat at reflux in a high boiling point solvent, for about 20 to 60 minutes. Such solvents are chemically stable, high boiling point solvents having a boiling point of 250 to 300° C. Diphenyl ether, α-chloronaphthalene, methyl α-naphthyl ether, ethyl α-naphthyl ether and dibenzyl ether are preferable.

Step (g)

The oxidizing agents may be selected from any of a variety of the agents known in the art of synthetic organic chemistry, for example, but not limited to, chromic acid (VI), pyridinium dichromate, pyridinium chlorochromate, chromium oxide (VI)—pyridine complex, manganese dioxide, dimethyl sulfoxide, hypohalorite and ruthenium tetraoxide.

Depending on the oxidizing agent and solvent used, the reaction may be carried out at a temperature of about 0 to 30° C., for about 1 to 10 hrs. The reaction solvents which may be used are any solvent if it is liquid in the neighborhood of the reaction temperature and is stable to the oxidizing agent. Halogenated hydrocarbons are preferable, such as dichloromethane, 1,2-dichloroethane and chloroform.

Step (h)

The reducing agents may be selected from any of a variety of the agents known in the art of synthetic organic chemistry, for example, but not limited to, diisobutylaluminum hydride, lithium aluminum hydride, triisobutylaluminum, trialkoxy derivatives of lithium aluminum hydroxide, sodium bis(2-methoxyethoxy)aluminum hydride, sodium borohydride, trimethoxy sodium borohydride, lithium borohydride, tri-sec-butyl lithium borohydride and tri-sec-butyl potassium borohydride.

Depending on the reducing agent and solvent used, the reaction may be carried out at a temperature of about −78 to 0° C., for about 1 to 5 hrs. The reaction solvents which may be used are any solvent if it is liquid at low temperature and is stable to the reducing agent. Toluene, benzene and THF are preferable.

Step (i)

The Mitsunobu reaction used here refers to condensation of alcohols and acidic components on treatment with dialkyl azodicarboxylates and trialkyl- or triarylphosphines occurring primarily with inversion of configuration via the proposed intermediary oxyphosphonium salts (see, Organic Name Reactions attached to The Merck Index, 12 Edn.)

Depending on the reactant and solvent used, the reaction may be carried out at a temperature between 0° C. and room temperature, for about 4 to 12 hrs. The reaction solvents which may be used are any solvent if it is good solvent inert to the starting compound used in the Mitsunobu reaction and the resulting compound, and is liquid in the neighborhood of the reaction temperature. THF and 1,3-dioxane are preferable.

The deprotection in step (i) can be carried out in conventional manner.

The present invention also provides a process for preparing an optically active compound of formula (1')

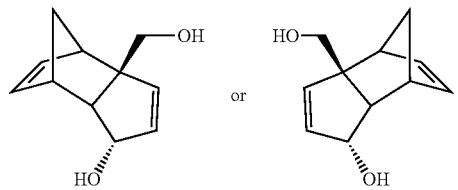

(1')

which comprises subjecting a racemic compound of formula (11)

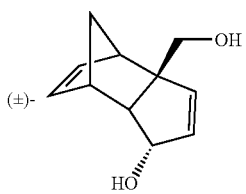

(11)

to a transesterification with an acylating agent in the presence of a hydrolase to optically resolve the racemic compound into an optically active diester of formula (12)

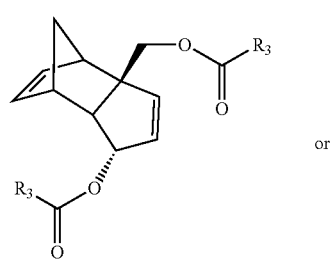

(12)

-continued

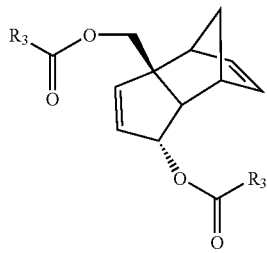

wherein $R_3$ is an alkyl group of 1–19 carbons, and a monoester of formula (13)

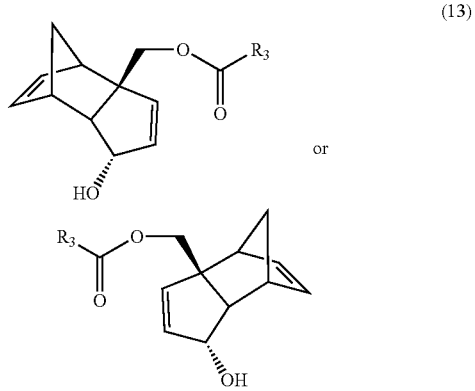

(13)

wherein $R_3$ is as defined above, followed by alcoholysis.

The transesterification can be carried out under conventional conditions with an acylating agent which has an acyl group of $R_3COO$ ($R_3$ is an alkyl group of 1–19 carbons) in the presence of a hydrolase. Examples of the alkyl groups of 1–19 carbons include, but are not limited to, methyl, ethyl, propyl, isopropyl, butyl, sec-butyl, tert-butyl, pentyl, heptyl, octyl, nonyl, dodecyl, tridecyl, tetradecyl, pentadecyl, hexadecyl, heptadecyl, octadecyl and nonadecyl.

PREFERRED EMBODIMENTS OF THE INVENTION

The processes of the present invention can be performed as discussed below. When the designated compounds show either one of enantiomers in the optically active compounds, it is marked with the prime mark (') except for the case of the compound (1').

The compound of formula (11) in a racemic form which can be used as a starting material in the present processes may be prepared by reducing the compound (16) prepared by Zwanenburg et al.'s method (Tetrahedron, 1985, 41, 963). As shown in the following scheme A, the compound (16) may be prepared by epoxidizing the compound (14) with aqueous hydrogen peroxide followed by a Favorskii rearrangement. The Favorskii rearrangement refers to a base-catalyzed rearrangement of α-haloketones or α,β-epoxyketones to acids or esters. The compound (14) is formed from a Diels-Alder reaction of cyclopentadiene and 1,4-benzoquinone which are easily available. The compound (16) is reduced with diisobutylaluminum hydride (DIBAL), thus leading to the compound (11).

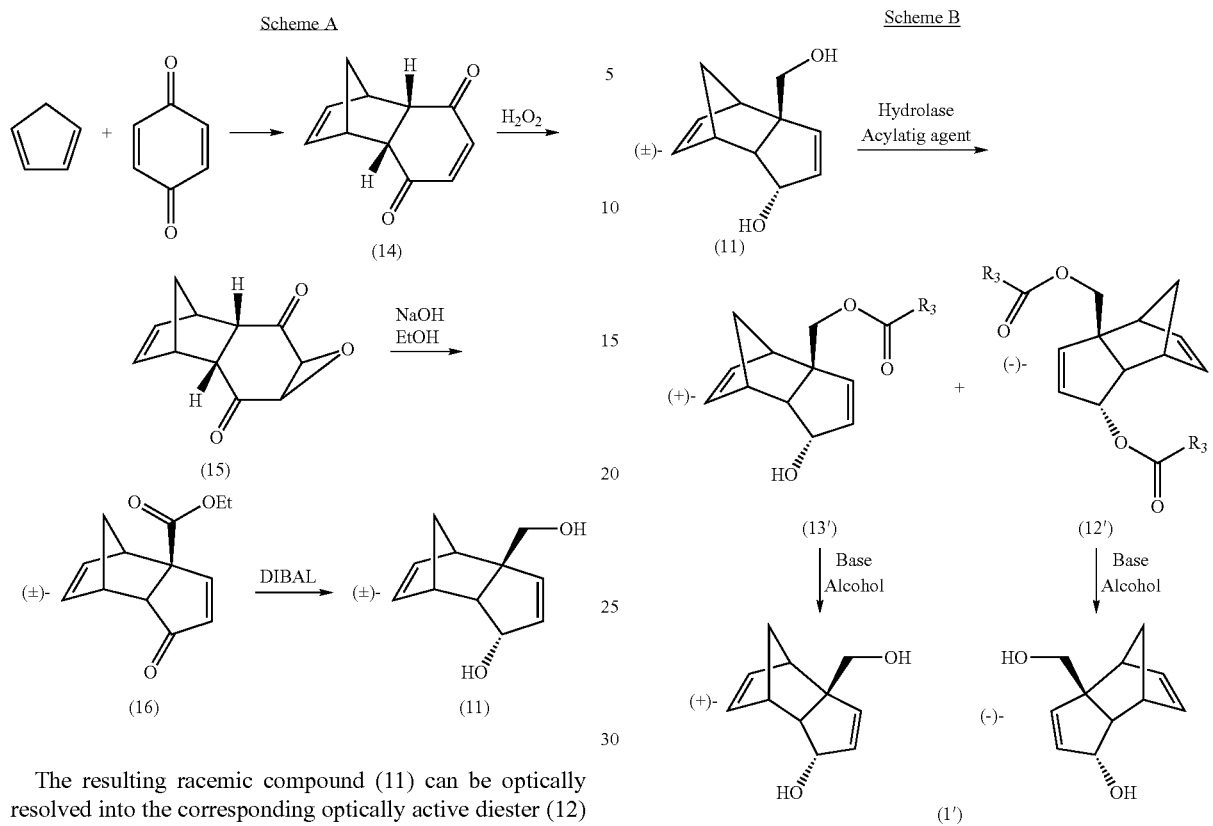

Scheme A

Scheme B

The resulting racemic compound (11) can be optically resolved into the corresponding optically active diester (12) and monoester (13), by the transesterification with the acylating agent in the presence of the hydrolase. The hydrolases which can be used herein, include, but are not limited to, lipase, esterase, protease and lipoprotein lipase. Those hydrolases may be any of animal, plant and fungus origins and may be commercially available immobilized products or dried extracts. Those originated from *pseudomonas, candida* and *pancreatin* are preferable. The acylating agents which can be used in the present process include, but are not limited to, fatty acid anhydrides, fatty acid esters or the like. More specifically, triglyceride, acetic anhydride, fatty acid trichloroethyl esters, fatty acid isopropenyl esters and fatty acid vinyl esters can be used, and fatty acid vinyl esters are especially preferable. The reaction solvents which can be used include ethers, alkanes, benzene derivatives, halogenated hydrocarbon solvents, e.g., acetonitrile, acetone, dimethylformamide (DMF), dimethyl sulfoxide (DMSO), diethyl ether, diisopropyl ether and t-butyl methyl ether. Diethyl ether, diisopropyl ether and t-butyl methyl ether are preferable. The reaction temperature is in the range of −20° C. to 200° C., preferably 20° C. to 40° C. The reaction time is in the range of 1 to 20 hrs., preferably 5 to 8 hrs. The treatment for purification after reaction can use general separation method such as silica gel column chromatography after the hydrolase is filtered off, by which each compound can be isolated and obtained.

As shown in the following scheme B, the resulting optically active diester (12') and monoester (13') can be subjected to the alcoholysis with an alcohol e.g., methanol in the presence of a suitable base such as potassium carbonate, thus leading to the optically active diol (1').

The (+)-form of the resulting diol (1') can lead to (−)-neplanocin A, and the (−)-form of the diol (1') can lead to (+)-neplanocin A.

The process for preparing (−)-neplanocin A is discussed below, but (+)-neplanocin A which is its enantiomer can be prepared in a similar manner, starting from the (−)-form of the diol (1').

The (+)-form of the diol (1') is reacted with a brominating agent such as N-bromosuccinimide to afford (+)-9-bromo-2-hydroxymethyl-5,8-epoxytricyclo[5.2.1.0$^{2,6}$]dec-3-ene (2a'). It is preferable that the reaction solvent uses halogenated hydrocarbon solvents such as dichloromethane. The reaction temperature is in the range of −20° C. to 20° C., preferably about 0° C. The reaction time is in the range of 1 to 10 hrs., preferably 2 hrs.

The above compound (2a') and t-butyldimethylsilyl chloride are reacted for 10–20 hrs in the presence of a suitable base such as imidazole to afford (+)-9-bromo-2-t-butyldimethylsilyloxymethyl-5,8-epoxytricyclo[5.2.1.0$^{2,6}$]dec-3-ene (3a') wherein the primary hydroxyl group in the compound (2a') is protected with t-butyldimethylsilyl group.

The compound (3a'), because of taking a cage stereostructure, can be treated with a suitable oxidizing agent such as osmium tetraoxide, thus leading stereoselectively and regiospecifically to (+)-9-bromo-2-t-butyldimethylsilyloxymethyl-3,4-dihydroxy-5,8-epoxytricyclo[5.2.1.0$^{2,6}$]decane (4a').

The reaction of two hydroxyl groups newly formed in said compound (4a') with dimethoxypropane affords (+)-9-bromo-2-t-butyldimethylsilyloxymethyl-3,4-[(dimethylmethylene)dioxy]-5,8-epoxytricyclo[5.2.1.0$^{2,6}$]decane (5a').

The compound (5a') is treated with active zinc powder to afford (+)-2-t-butyldimethylsilyloxymethyl-3,4-[(dimethylmethylene)dioxy]-5-hydroxy-tricyclo[5.2.1.0$^{2,6}$]dec-8-ene (6a').

The compound (6a') can be heated to reflux in diphenyl ether or can be subjected to a flush vacuum thermolysis to induce a retro-Diels-Alder reaction, thus leading to (−)-(1R,4R,5S)-3-(t-butyldimethylsilyloxymethyl)-4,5-[(dimethylmethylene)dioxy]-2-cyclopentene-1-ol (7a').

The treatment of the hydroxyl group in the compound (7a') with a suitable oxidizing agent such as pyridinium dichromate and pyridinium chlorochromate affords (−)-(4R,5S)-3-(t-butyldimethylsilyloxymethyl)-4,5-[(dimethylmethylene)dioxy]-2-cyclopentene-1-one (8a').

Reduction of the compound (8a') with a reducing agent such as diisobutyl aluminum hydride, lithium aluminum hydride or the like can lead stereospecifically to (+)-(1S,4R,5S)-3-(t-butyldimethylsilyloxymethyl)-4,5-[(dimethylmethylene)dioxy]-2-cyclopentene-1-ol (9a') wherein the hydroxyl group at the 1-position of the compound (7a') is inversed.

Combining the compound (9a') with adenine by a Mitsunobu reaction can lead to (−)-(1'R,4'R,5'S)-3'-(t-butyldimethylsilyloxymethyl)-4',5'-[(dimethylmethylene)-dioxy]-2'-cyclopentene-1'-yl]adenine (10a'). Finally, the compound (10a') is deprotected using a purification method with an ion-exchange resin to afford (−)-neplanocin A.

The invention is further illustrated by the following Examples. These examples are presented to exemplify the invention and are not to be construed as limiting the invention's scope.

REFERENTIAL EXAMPLE 1

A solution of tricyclo[6.2.1.0$^{2,7}$]undeca-4,9-diene-3,6-dione (14) (26.13 g, 150 mmol) in acetone (100 ml) was cooled to 0° C. on an ice-bath. To the solution was added saturated aqueous NaHCO$_3$ (33 ml). To the mixture was added dropwise 34.5% aqueous hydrogen peroxide (142 ml) while keeping at 0° C. After the addition, the reaction mixture was stirred at 0° C. for 1 hr and then water (100 ml) was added. From the mixture solution, the product was extracted with diethyl ether (total 700 ml). The extract was washed with saturated aqueous NaCl and dried over magnesium sulfate, and the solvent was distilled off under reduced pressure to afford as the residue 4,5-epoxy-tricyclo[6.2.1.0$^{2,7}$]undec-9-ene-3,6-dione (15) (28.06 g, 148 mmol, 98.35% yield) in light yellowish white crystals.

REFERENTIAL EXAMPLE 2

A suspension of 4,5-epoxy-tricyclo[6.2.1.0$^{2,7}$]undec-9-ene-3,6-dione (15) (9.28 g, 48.8 mmol) in ethanol (50 ml) was heated to 45° C. To the suspension was added dropwise a 5 M-ethanol solution of sodium hydroxide (18 ml) over a period of 30 minutes. From the reaction mixture, ethanol was distilled off under reduced pressure. The residue was dissolved with diethyl ether (300 ml), washed with saturated aqueous NaCl and dried over magnesium sulfate, and diethyl ether was distilled off under reduced pressure to afford as the residue 5-oxo-tricyclo[5.2.1.0$^{2,6}$]deca-3,8-diene-2-carboxylate (16) (6.58 g, 30.1 mmol, 61.78% yield) in dark brown liquid.

EXAMPLE 1

A solution of ethyl 5-oxo-tricyclo[5.2.1.0$^{2,6}$]deca-3,8-diene-2-carboxylate (16) (1.84 g, 8.43 mmol) in toluene (30 ml) was cooled to −78° C. under an argon atmosphere and stirred. To the reaction solution was added dropwise a 1.5 M-toluene solution of diisobutylaluminum hydride (DIBAL) (19.7 ml, 29.5 mmol) over a 25 minute period. The reaction mixture was stirred for 3 hrs while keeping at −78° C. and aqueous ammonia was added while cooling. The precipitated solid was filtered off through a glass funnel. The filtrate was concentrated under reduced pressure to afford 2.08 g of the residue (white solid) which was then subjected to silica gel column chromatography (eluting solvent: n-hexane/ethyl acetate=1/1) to afford 2-hydroxymethyl-5-hydroxy-tricyclo[5.2.1.0$^{2,6}$]deca-3,8-diene (11) (0.98 g, 5.5 mmol, 65% yield), with the following data:

IR (neat): ν=3270 cm$^{-1}$ $^1$H NMR (CDCl$_3$): δ=1.60 (1H, d, J=8.8 Hz), 1.68 (1H, d, J=8.8 Hz), 2.70 (2H, m), 2.96 (1H, s), 3.67 (1H, d, J=10.6 Hz), 3.84 (1H, d, J=10.6 Hz), 4.76 (1H, s), 5.53 (1H, dd, J=5.5, 1.8 Hz).

EXAMPLE 2

A suspension of 2-hydroxymethyl-5-hydroxy-tricyclo[5.2.1.0$^{2,6}$]deca-3,8-diene (11) (980 mg, 5.5 mmol) and vinyl acetate (758 mg, 8.8 mmol) in t-butyl methyl ether (3 ml) was stirred at room temperature. To the reaction solution was added lipase (1 g, immobilized lipase originated from *pseudomonas*, manufactured by Toyobo Co., Ltd.) and the mixture was stirred at room temperature for 8 hrs. Lipase was filtered off and the filtrate was concentrated under reduced pressure to afford a yellow residue. The residue was subjected to silica gel column chromatography (eluting solvent: n-hexane/ethyl acetate=3/1) to afford the diacetate (12') (590 mg, 2.25 mmol) and the monoacetate (13') (495 mg, 2.25 mmol), respectively, with the following data:

For (−)-diacetate (12')

IR (neat): ν=2967, 1734 cm$^{-1}$ $^1$H NMR (CDCl$_3$): δ=1.52 (1H, d, J=8.8 Hz), 1.60 (1H, d, J=8.8 Hz), 1.99 (3H, s), 2.01 (3H, s), 2.69 (1H, br s), 2.74 (1H, br s), 4.07 (1H, d, J=10.7 Hz), 4.34 (1H, d, J=10.7 Hz), 5.50 (2H, m), 5.95 (2H, m) MS: m/z=262 (M+). Anal. Calcd. for C15H18O4 (M+): m/z=262.1205. Found: m/z=262.1203.

For (+)-monoacetate (13')

IR (neat): ν=3440, 2962, 1730 cm$^{-1}$ $^1$H NMR (CDCl$_3$): δ=1.60 (1H, d, J=8.8 Hz), 1.68 (1H, d, J=8.8 Hz), 2.05 (3H, s), 2.64 (1H, m), 2.78 (1H, br s), 2.94 (1H, br s), 4,12 (1H, d. J=10.7 Hz), 4.36 (1H, d, J=10.7 Hz), 4.76 (1H, d, J=10.2 Hz), 5.54 (1H, d, J=1.4 Hz), 5.59 (1H, d, J=1.4 Hz), 5.92 (1H, m), 6.16 (1H, m) MS: m/z=220 (M+). Calcd. for C13H16O3 (M+): m/z=220.1099. Found: m/z=220.1104.

To a solution of the resultant diacetate (12') (590 mg) in methanol (20 ml) was added potassium carbonate (691 mg, 5.0 mmol) and the mixture was stirred at room temperature for 8 hrs. The reaction product was extracted with ethyl acetate (40 ml). The organic layer was washed with saturated aqueous NaCl, dried over magnesium sulfate and concentrated under reduced pressure to afford (−)-2-hydroxymethyl-5-hydroxy-tricyclo[5.2.1.0$^{2,6}$]deca-3,8-diene (330 mg, 1.85 mmol) having the following specific rotation:

[α]$_D^{26}$ −168.11° (cl. 03, EtOH).

According to a conventional method, further, this compound was led to the dibenzoate which was analyzed with an optical resolution column (Chiral Cell OD manufactured by Daicel Co., Ltd., 5%-isopropanol-n-hexane solution), by which it was found 92% ee.

For the monoacetate (13'), similar procedure was carried out except for using 373 mg (2.7 mmol) of potassium carbonate, thereby affording (+)-2-hydroxymethyl-5-hydroxy-tricyclo[5.2.1.0$^{2,6}$]deca-3,8-diene (367 mg, 2.06 mmol) having the following specific rotation and melting point:

[α]$_D^{30}$ +154.860° (cl. 01, EtOH), m.p. 116–119° C.

According to a conventional method, further, this compound was led to the dibenzoate which was analyzed with an optical resolution column (Chiral Cell OD manufactured by Daicel Co., Ltd., 5%-isopropanol-n-hexane solution), by which it was found >99% ee.

EXAMPLE 3

A solution of (+)-2-hydroxymethyl-5-hydroxy-tricyclo [5.2.1.0$^{2,6}$]deca-3,8-diene ((+)-form of Compound (1')) (287 mg, 1.6 mmol) obtained in Example 2 in dichloromethane (30 ml) was cooled to 0° C. and stirred. To the solution was added N-bromosuccinimide (322 mg, 1.8 mmol) and the mixture was stirred for 2 hrs while keeping at 0° C. The reaction solution was concentrated under reduced pressure and the resulting residue was subjected to silica gel column chromatography (eluting solvent: n-hexane/ethyl acetate=2/1) to afford (+)-9-bromo-2-hydroxymethyl-5,8-epoxytricyclo-[5.2.1.0$^{2,6}$]dec-3-ene (2a') (414 mg, 1.6 mmol, 99.6% yield), with the following data:

[α]$_D^{29}$ +153.15° (c0.302, CHCl$_3$) IR (neat): ν=3409, 2972 cm$^{-1}$ $^1$H NMR (CDCl$_3$): δ=1.73 (1H, br), 2.17–2.38 (1H, m), 3.48 (2H, d), 4.08 (1H, d), 4.56–4.69 (3H, m), 5.70 (1H, m), 6.0 (1H, m) MS: m/z=256 (M+). Calcd. for C11H13BrO2 (M+): m/z=256.0098. Found: m/z=256.0112.

EXAMPLE 4

To a solution of (+)-9-bromo-2-hydroxymethyl-5,8-epoxytricyclo[5.2.1.0$^{2,6}$]dec-3-ene (2a') (319 mg, 1.24 mmol) and imidazole (126.5 mg, 1.86 mmol) in DMF (30 ml) was added t-butyldimethylsilyl chloride (242 mg, 1.6 mmol), and the mixture was stirred overnight at room temperature and diluted with n-hexane (80 ml). The organic layer was washed with saturated aqueous NaCl, dried over magnesium sulfate and concentrated under reduced pressure to obtain the residue. Silica gel column chromatography (eluting solvent: n-hexane/diethyl ether=2/1) of the residue afforded (+)-9-bromo-2-(t-butyldimethyl silyloxymethyl)-5,8-epoxytricyclo[5.2.1.0$^{2,6}$]dec-3-ene (3a') (447 mg, 1.20 mmol, 97% yield), with the following data:

[α]$_D^{28}$ +114.06° (c0.161, CHCl$_3$) IR (neat): ν=2954, 2856, 1471, 1377 cm$^{-1}$ $^1$H NMR (CDCl$_3$): δ=0.013 (6H, s), 0.86 (9H, s), 2.16–2.38 (2H, m), 2.39–2.65 (3H, m), 3.40 (1H, d, J=10.0 Hz), 3.77 (1H, d, J=10.0 Hz), 4.13 (1H, d, J=2.5 Hz), 4.61 (2H, m), 5.77 (1H, d, J=5.7 Hz), 5.95 (1H, dd, J=5.7, 2.5 Hz) MS: m/z=355 (M+ −Me). Calcd. for C16H24BrO2Si (M+ −Me): m/z=355.0763. Found: m/z=355.0729.

EXAMPLE 5

A solution of (+)-9-bromo-2-(t-butyldimethylsilyloxymethyl)-5,8-epoxytricyclo[5.2.1.0$^{2,6}$]dec-3-ene (3a') (283 mg, 0.762 mmol) in a mixed solvent of THF (15 ml) and water (5 ml) was cooled to 0° C. and stirred. To the solution were added 4-methylmorpholine N-oxide (155 mg, 1.14 mmol) and a 0.197 M-THF solution of osmium tetraoxide (1.5 ml, 0.3 mmol). Subsequently, the mixture was allowed to warm up to room temperature and stirred overnight. A 10% aqueous solution of sodium sulfite (15 ml) was added and the mixture was filtered through Celite. The filtered product was washed thoroughly with water, THF and diethyl ether. The combined washings and filtrate were diluted with diethyl ether (80 ml). The organic layer was washed with saturated aqueous NaHCO$_3$ and saturated aqueous NaCl, respectively, and dried over magnesium sulfate. Subsequently, the solvent was distilled off under reduced pressure to obtain the residue. Silica gel column chromatography (eluting solvent: n-hexane/diethyl ether=2/1) of the residue afforded (+)-9-bromo-2-(t-butyldimethylsilyloxymethyl)-3,4-dihydroxy-5,8-epoxytricyclo[5.2.1.0$^{2,6}$]decane (4a') (246 mg, 0.607 mmol, 80% yield), with the following data:

[α]$_D^{28}$ +57.15° (c0.26, CHCl$_3$) $^1$H NMR (CDCl$_3$): δ=0, 099 (6H, s), 0.89 (9H, s), 1.65 (1H, brs), 1.95 (1H, d, J=10.9 Hz), 2.16–2.38 (2H, m), 2.37 (2H, m), 2.62 (1H, t, J=4.4 Hz), 2.77 (1H, m), 3.05 (1H, d, J=5.2 Hz), 3.51 (1H, d, J=5.5 Hz), 3.60 (1H, d, J=10.2 Hz), 3.81 (1H, d, J=9.9 Hz), 4.15 (2H, m), 4.39 (1H, t, J=4.9 Hz), 4 53 (1H, d, J=4.9 Hz) MS: m/z=389 (M+ −Me). Calcd. for C16H26BrO4Si (M+ −Me): m/z=389.0318. Found: m/z=389.0397.

EXAMPLE 6

To a solution of (+)-9-bromo-2-(t-butyldimethylsilyloxymethyl)-3,4-dihydroxy-5,8-epoxytricyclo[5.2.1.0$^{2,6}$]-decane (4a') (186 mg, 0.459 mmol) in acetone (30 ml) were added dimethoxypropane (72 mg, 0.69 mmol) and pyridinium p-toluenesulfonate (15 mg) and the mixture was stirred overnight at room temperature. To the reaction solution was added diethyl ether (50 ml) and the mixture was washed with saturated aqueous NaHCO$_3$ and saturated aqueous NaCl. This solution was dried over magnesium sulfate and concentrated under reduced pressure to obtain the residue. Silica gel column chromatography (eluting solvent: n-hexane/ethyl acetate=3/1) of the residue afforded (+)-9-bromo-2-(t-butyldimethylsilyloxymethyl)-3,4-[(dimethylmethylene)dioxy]-5,8 -epoxytricyclo[5.2.1.0$^{2,6}$]decane (5a') (205 mg, 0.46 mmol), 100% yield), with the following data:

[α]$_D^{29}$ +73.15° (c0.12, CHCl$_3$) IR (neat): ν=2928, 2855, 1471, 1380 cm$^{-1}$ $^1$H NMR (CDCl$_3$): δ=0.023 (6H, s), 0.86 (9H, s), 1.24 (3H, s), 1.41 (3H, s), 2.02–2.19 (2H, m), 2.36 (1H, m), 2.69 (1H, m), 3.47 (1H, d, J=9.9 Hz), 3.63 (1H, d, J=2.5 Hz), 3.98 (1H, d, J=9.6 Hz), 4.37 (1H, d, J=5.7 Hz), 4.54 (1H, m), 4.60 (1H, d, J=5.5 Hz) MS: m/z=429 (M+ −Me). Calcd. for C19H30BrO4Si (M+ −Me): m/z=429.1131. Found: m/z=429.1090.

EXAMPLE 7

To a solution of (+)-9-bromo-2-(t-butyldimethylsilyloxymethyl)-3,4-[(dimethylmethylene)dioxy]-5,8-epoxytricyclo[5.2.1.0$^{2,6}$]decane (5a') (205 mg, 0.46 mmol) in methanol (30 ml) were added active zinc powder (182 mg, 2.76 mmol) and acetic acid (0.1 ml), and the mixture was heated to reflux for 10 hrs. The reaction solution was filtered through Celite and the filtered mass was washed with methanol. The combined washings and filtrate were diluted with diethyl ether (80 ml) and washed with saturated aqueous NaHCO$_3$ and saturated aqueous NaCl. This solution was dried over magnesium sulfate and concentrated under reduced pressure to afford (+)-2-(t-butyldimethylsilyloxymethyl)-3,4-[(dimethylmethylene)dioxy]-5-hydroxy-tricyclo [5.2.1.0$^{2,6}$]-dec-8-ene (6a') (160 mg, 0.44 mmol, 95% yield) in colorless powdery crystals, with the following data:

[α]$_D^{30}$ +147.0° (c0.30, CHCl$_3$) IR (Nujol): ν=3313, 2924, 2854, 1462, 1376 cm$^{-1}$ $^1$H NMR (CDCl$_3$): δ=0.023 (6H, s), 0.87 (9H, s), 1.18 (3H, s), 1.41 (4H, m), 1.58 (1H, m), 1.78 (1H, brs), 2.40 (1H, m), 2.86 (1H, s), 3.05 (1H, s), 3.52 (1H, d, J=9.6 Hz), 3.99 (1H, d, J=4.9 Hz), 4.07–4.12 (3H, m), 6.20 (1H, m), 6.32 (1H, m) MS: m/z=366 (M+). Calcd. for C20H34O4Si (M+): m/z=366.2226. Found: m/z=366.2242.

EXAMPLE 8

A solution of (+)-2-(t-butyldimethylsilyloxymethyl)-3,4-[(dimethylmethylene)dioxy]-5-hydroxy-tricyclo[5.2.1.0$^{2,6}$]dec-8-ene (6a') (280 mg, 0.76 mmol) in diphenyl ether (5 ml) was heated to reflux for 30 minutes. The reaction solution was subjected to silica gel column chromatography (eluting solvent: n-hexane/diethyl ether=1/1) to afford (−)-(1R,4R,5S)-3-(t-butyldimethylsilyloxymethyl)-4,5-[(dimethylmethylene)dioxy]-2-cyclopenten-1-ol (7a') (225 mg, 0.749 mmol, 98.7% yield), with the following data:

$[\alpha]_D^{32}$ −21.53° (c0.54, CHCl$_3$) IR (neat): ν=3405, 2930, 2857, 1372 cm$^{-1}$ $^1$H NMR (CDCl$_3$): δ=0.086 (6H, s), 0.92 (9H, s), 1.36 (6H, d, J=11.2 Hz), 1.98 (1H, d, J=6.3 Hz), 4.33 (2H, m), 4.55 (1H, d, J=5.8 Hz), 4.72 (1H, m), 5.13 (1H, d, J=5.8 Hz), 5.75 (1H, d, J=1.1 Hz) MS: m/z=285 (M+ −Me). Calcd. for C14H25O4Si (M+ −Me): m/z=285.1557. Found: m/z=285.1502.

EXAMPLE 9

To a solution of (−)-(1R,4R,5S)-3-(t-butyldimethylsilyloxymethyl)-4,5-[(dimethylmethylene)dioxy]-2-cyclopenten-1-ol (7a') (225 mg, 0.749 mmol) in dichloromethane (50 ml) was added pyridinium dichromate (425 mg, 1.13 mmol) and the mixture was stirred at room temperature for 2 hrs. The reaction solution was filtered through Celite and the filtrate was concentrated under reduced pressure to obtain the residue. Silica gel column chromatography (eluting solvent: n-hexane/diethyl ether=1/1) of the residue afforded (−)-(4R,5S)-3-(t-butyldimethylsilyloxymethyl)-4,5-[(dimethylmethylene)dioxy]-2-cyclopenten-1-one (8a') (186 mg, 0.623 mmol, 83% yield), with the following data:

$[\alpha]_D^{29}$ −10.67° (c0.85, CHCl$_3$). IR (neat): ν=2955, 2931, 2857, 1725 cm$^{-1}$ $^1$H NMR (CDCl$_3$): δ=0.076 (6H, s), 0.89 (9H, s), 1.38 (6H, s), 4.41–4.68 (3H, m), 5.03 (1H, d, J=5.8 Hz), 6.14 (1H, t, J=1.9 Hz) MS: m/z=283 (M+ −Me). Calcd. for C14H23O4Si (M+ −Me): m/z=283.14. Found: m/z=283.1377.

EXAMPLE 10

A solution of (−)-(4R,5S)-3-(t-butyldimethylsilyloxymethyl)-4,5-[(dimethylmethylene)dioxy]-2-cyclopenten-1-one (8a') (186 mg, 0.623 mmol) in toluene (10 ml) was cooled to −78° C. To the solution was added dropwise a 1.5 M-toluene solution of diisobutylaluminum hydride (0.62 ml, 0.93 mmol), and the mixture was stirred at −78° C. for 2 hrs. The reaction solution diluted with methanol and water, respectively was extracted with chloroform. The organic layer was washed with saturated aqueous NaCl, dried over magnesium sulfate and concentrated under reduced pressure. The residue was subjected to silica gel column chromatography (eluting solvent: n-hexane/diethyl ether=1/1) to afford (+)-(1S,4R,5S)-3-(t-butyldimethylsilyloxymethyl)-4,5-[(dimethylmethylene)dioxy]-2-cyclopenten-1-ol (9a') (186 mg, 0.62 mmol, 100% yield), with the following data:

$[\alpha]_D^{29}$ +22.53° (c0.63, CHCl$_3$). IR (neat): ν=2954, 2930, 2857, 1372 cm$^{-1}$ $^1$H NMR (CDCl$_3$): δ=0.05 (6H, s), 0.89 (9H, s), 1.38 (6H, d, J=8.8 Hz), 2.65 (1H, d, J=10.2 Hz), 4.17–4.35 (2H, m), 4.52 (1H, m), 4.74 (1H, m), 4.87 (1H, m), 5.71 (1H, t, J=0.8 Hz) MS: m/z=285 (M+ −Me). Calcd. for C14H25O4Si (M+ −Me): m/z=285.1557. Found: m/z=285.1529.

EXAMPLE 11

A solution of (+)-(1S,4R,5S)-3-(t-butyldimethylsilyloxymethyl)-4,5-[(dimethylmethylene)dioxy]-2-cyclopenten-1-ol (9a') (145 mg, 0.48 mmol), adenine (272 mg, 1.92 mmol) and triphenylphosphine (529 mg, 2.02 mmol) in THF (90 ml) was cooled to 0° C. To the cooled solution was added dropwise diisopropyl azodicarboxylate (408 mg, 2.02 mmol), and the mixture was allowed to warm up to room temperature and stirred for 8 hrs. The reaction solution was concentrated under reduced pressure and the resulting residue was subjected to silica gel column chromatography (eluting solvent: chloroform/ethanol=10/1) to afford (−)-[(1'R,4'R,5'S)-3'-(t-butyldimethylsilyloxymethyl)-4',5'-[(dimethylmethylene)dioxy]-2'-cyclopentene-1'-yl]adenine (10a') (148 mg, 0.40 mmol, 84% yield), with the following data:

$[\alpha]_D^{29}$ −31.57° (c0.29, CHCl$_3$) IR (neat): ν=3322, 3171, 2954, 2931, 2857, 1645, 1597 cm$^{-1}$ $^1$H NMR (CDCl$_3$): δ=0.10 (6H, s), 0.92 (9H, s), 1.35 (3H, s), 1.48 (3H, s), 4.43 (2H, m), 4.70 (1H, d, J=5.8 Hz), 5.31 (1H, d, J=5.2 Hz), 5.59 (1H, m), 5.75 (1H, s), 5.78 (2H, brs), 7.68 (1H, s), 8.39 (1H, s) MS: m/z=412 (M+ −Me). Calcd. for C19H28N5O3Si (M+ −Me): m/z=402.1996. Found: m/z=402.1935.

EXAMPLE 12

A solution of (−)-[(1'R,4'R,5'S)-3'-(t-butyldimethylsilyloxymethyl)-4',5'-[(dimethylmethylene)-dioxy]-2'-cyclopentene-1'-yl]adenine (10a') (138 mg, 0.33 mmol) in a mixed solvent of methanol (20 ml) and 1N-hydrochloric acid (20 ml) was stirred at room temperature for 3 hrs. The reaction solution was concentrated under reduced pressure, and the resulting residue was dissolved in water (1 ml) and passed through an ion exchange resin column (Dowex 50, H$^+$ form). This column was washed by passing pure water therethrough and then eluted with 5% aqueous ammonia. The resulting eluate was concentrated under reduced pressure to obtain white crystals. Recrystallization from methanol afforded (−)-Neplanocin A (78 mg, 0.30 mmol, 90% yield), with the following physical values:

$[\alpha]_D^{29}$ −31.57° (c0.29, CHCl$_3$), m.p. 217–219° C.

These values agreed closely with those given in the literature.

INDUSTRIAL APPLICABILITY

According to the present invention, there can be prepared optically active 2-hydroxymethyl-5-hydroxy-tricyclo[5.2.1.0$^{2,6}$]deca-3,8-diene (1') which is a chiral element useful in the organic synthesis. The present invention can also provide the process for efficiently preparing neplanocin A in 10 steps and in 45% overall yield, starting from the compound (1').

What is claimed is:

1. A compound of formula (2)

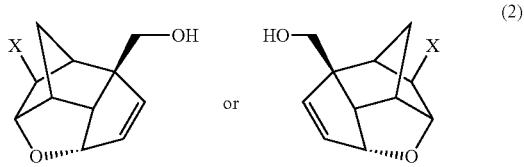

wherein X is halogen.

2. A compound of claim 1 wherein x is Br.

* * * * *